(12) United States Patent
Charles et al.

(10) Patent No.: US 6,676,669 B2
(45) Date of Patent: Jan. 13, 2004

(54) SURGICAL MANIPULATOR (75) Inventors: Steve T. Charles, Germantown, TN (US); J. Michael Stuart, Corrales, NM (US); Larry Bronisz, Los Alamos, NM (US)

(73) Assignee: MicroDexterity Systems, Inc., Memphis, TN (US)

(*) Notice: Subject to any disclaimer, the term of this patent is extended or adjusted under 35 U.S.C. 154(b) by 166 days.

(21) Appl. No.: 10/050,241

(22) Filed: Jan. 16, 2002

(65) Prior Publication Data
US 2002/0133174 A1 Sep. 19, 2002

Related U.S. Application Data
(60) Provisional application No. 60/261,940, filed on Jan. 16, 2001.

(51) Int. Cl.$^7$ .............................................. A61B 19/00
(52) U.S. Cl. ............................ 606/130; 606/1; 901/48
(58) Field of Search ................... 606/130, 1; 600/229, 600/102, 407, 417; 604/116; 378/20, 163; 700/245; 901/2, 30, 14, 48, 41; 128/898

(56) References Cited

U.S. PATENT DOCUMENTS

| | | |
|---|---|---|
| 3,923,166 A | 12/1975 | Fletcher et al. |
| 3,949,747 A | 4/1976 | Hevesy |
| 4,401,433 A | 8/1983 | Luther |
| 4,573,452 A | 3/1986 | Greenberg |
| 4,653,509 A | 3/1987 | Oloff et al. |
| 4,849,692 A | 7/1989 | Blood |
| 4,945,305 A | 7/1990 | Blood |
| 5,053,687 A | 10/1991 | Merlet |
| 5,078,140 A | 1/1992 | Kwoh |
| 5,081,381 A | 1/1992 | Narasaki |
| 5,086,401 A | 2/1992 | Glassman et al. |
| 5,142,930 A | 9/1992 | Allen et al. |
| 5,161,542 A | 11/1992 | Palestrant |
| 5,184,601 A | 2/1993 | Putman |
| 5,186,174 A | 2/1993 | Schlondorff et al. |
| 5,234,000 A | 8/1993 | Hakky et al. |
| 5,240,011 A | 8/1993 | Assa |
| 5,243,266 A | 9/1993 | Kasagami et al. |
| 5,251,127 A | 10/1993 | Raab |
| 5,269,034 A | 12/1993 | Day et al. |
| 5,273,039 A | 12/1993 | Fujiwara et al. |
| 5,279,309 A | 1/1994 | Taylor et al. |
| 5,280,427 A | 1/1994 | Magnusson et al. |
| 5,299,288 A | 3/1994 | Glassman et al. |
| 5,305,203 A | 4/1994 | Raab |
| 5,307,072 A | 4/1994 | Jones, Jr. |
| 5,343,385 A | 8/1994 | Joskowicz et al. |
| 5,354,158 A | 10/1994 | Sheldon et al. |
| 5,383,454 A | 1/1995 | Bucholz |

(List continued on next page.)

FOREIGN PATENT DOCUMENTS

| | | |
|---|---|---|
| EP | 0009447 A1 | 4/1980 |
| WO | WO/9910137 A1 | 3/1999 |
| WO | WO/002882 A2 | 5/2000 |
| WO | WO/0030557 A1 | 6/2000 |

OTHER PUBLICATIONS

International Search Report (Jun. 2002).
Shai–Syg Motion & Innovations Ltd.; Robolite; copy of internet home page. Applicants first became aware of this material in Jun. 1998.
MicroE Inc.; copies of internet brochure pages of Rotary Micro Encoder and Linear Micro Encoder. Applicants first became aware of this material in Aug. 1998.

*Primary Examiner*—Pedro Philogene
(74) *Attorney, Agent, or Firm*—Leydig, Voit & Mayer, Ltd.

(57) ABSTRACT

The present invention provides a surgical manipulator which capable of manipulating a surgical or medical tool in up to six degrees of freedom. The manipulator has a relatively lightweight, compact design as a result of the use of high force to mass ratio actuators. The manipulator includes a mounting fixture which permits the manipulator to be fixed relative to a portion of a body of a patient.

55 Claims, 8 Drawing Sheets

U.S. PATENT DOCUMENTS

| | | | |
|---|---|---|---|
| 5,389,101 A | | 2/1995 | Heilbrun et al. |
| 5,397,323 A | * | 3/1995 | Taylor et al. ............... 606/130 |
| 5,402,801 A | | 4/1995 | Taylor |
| 5,408,409 A | | 4/1995 | Glassman et al. |
| 5,415,182 A | | 5/1995 | Chin et al. |
| 5,417,210 A | | 5/1995 | Funda et al. |
| 5,425,616 A | | 6/1995 | Arai et al. |
| 5,445,166 A | | 8/1995 | Taylor |
| 5,453,686 A | | 9/1995 | Anderson |
| 5,464,013 A | | 11/1995 | Lemelson |
| 5,494,034 A | | 2/1996 | Schlondorff et al. |
| 5,564,436 A | | 10/1996 | Hakky et al. |
| 5,564,663 A | | 10/1996 | Cook et al. |
| 5,568,593 A | | 10/1996 | Demarest et al. |
| 5,572,999 A | | 11/1996 | Funda et al. |
| 5,584,292 A | | 12/1996 | Cheung |
| 5,600,330 A | | 2/1997 | Blood |
| 5,628,327 A | | 5/1997 | Unger et al. |
| 5,630,431 A | | 5/1997 | Taylor |
| 5,640,170 A | | 6/1997 | Anderson |
| 5,643,286 A | | 7/1997 | Warner et al. |
| 5,647,373 A | | 7/1997 | Patieli |
| 5,676,673 A | | 10/1997 | Ferre et al. |
| 5,695,500 A | | 12/1997 | Taylor et al. |
| 5,744,953 A | | 4/1998 | Hansen |
| 5,748,767 A | | 5/1998 | Raab |
| 5,749,362 A | | 5/1998 | Funda et al. |
| 5,767,669 A | | 6/1998 | Hansen et al. |
| 5,776,153 A | | 7/1998 | Rees |
| 5,782,764 A | | 7/1998 | Werne |
| 5,795,291 A | | 8/1998 | Koros |
| 5,800,352 A | | 9/1998 | Ferre et al. |
| 5,800,423 A | | 9/1998 | Jensen |
| 5,803,089 A | | 9/1998 | Ferre et al. |
| 5,803,912 A | | 9/1998 | Siczek et al. |
| 5,806,518 A | | 9/1998 | Mittelstadt |
| 5,807,378 A | | 9/1998 | Jensen et al. |
| 5,817,084 A | | 10/1998 | Jensen |
| 5,829,444 A | | 11/1998 | Ferre et al. |
| 5,833,656 A | | 11/1998 | Smith et al. |
| 5,851,183 A | | 12/1998 | Bucholz |
| 5,865,744 A | | 2/1999 | Lemelson |
| 5,873,822 A | | 2/1999 | Ferre et al. |
| 5,887,121 A | | 3/1999 | Funda et al. |
| 5,943,914 A | | 8/1999 | Morimoto et al. |
| 5,950,629 A | | 9/1999 | Taylor et al. |
| 5,951,475 A | | 9/1999 | Gueziec et al. |
| 5,967,980 A | | 10/1999 | Ferre et al. |
| 5,976,156 A | | 11/1999 | Taylor et al. |
| 6,000,297 A | | 12/1999 | Morimoto et al. |
| 6,021,342 A | | 2/2000 | Brabrand |
| 6,024,695 A | | 2/2000 | Taylor et al. |
| 6,138,495 A | | 10/2000 | Paltieli et al. |
| 6,309,397 B1 | | 10/2001 | Julian et al. |
| 6,406,472 B1 | * | 6/2002 | Jensen ........................ 606/1 |
| 6,413,264 B1 | * | 7/2002 | Jensen et al. ............... 606/130 |
| 6,491,701 B2 | * | 12/2002 | Tierney et al. .............. 606/130 |

* cited by examiner

SURGICAL MANIPULATOR

CROSS-REFERENCE TO RELATED APPLICATION

This application claims the benefit of U.S. Provisional Application No. 60/261,940, filed Jan. 14, 2001 which is incorporated herein by reference.

FIELD OF THE INVENTION

The present invention relates to manipulators and, more particularly to a manipulator suitable for use in medical procedures, including surgical procedures.

BACKGROUND OF THE INVENTION

Conventional devices which are used to perform very complex and/or physically demanding surgical procedures like neurosurgery, spine surgery, ear surgery, head and neck surgery, hand surgery and minimally invasive surgical procedures have a number of drawbacks as it relates to the dexterity of the surgeon. For example, the surgeon can easily become fatigued by the need to manually support the surgical device during its use. Additionally, the surgeon may have to orient his hands in an awkward position in order to operate the device. Furthermore, conventional devices used in such surgical procedures can produce angular magnification of errors. As a result, a surgeon has considerably less dexterity and precision when performing an operation with such surgical devices than when performing an operation by traditional techniques in which the surgeon grasps a tool directly.

Accordingly, there is an increasing interest in the use of powered manipulators, such as robotic and master-slave manipulators for supporting and manipulating surgical tools during medical procedures. Such manipulators can provide a number of advantages to both patients and medical practitioners. In particular, a master/slave controlled manipulator can enhance the dexterity of the surgeon/operator so as to allow the surgeon to manipulate a medical tool with greater dexterity than he could if he was actually holding the tool in his hands. A manipulator can also reduce the fatigue experienced by a surgeon, since it eliminates the need for the surgeon to physically support the medical tool or device during its use. Additionally, the surgeon can let go of the manipulator and perform other tasks without the medical tool undergoing movement, which increases the efficiency of the surgeon and can reduce the number of individuals that are necessary to perform a particular procedure. Thus, manipulators can allow medical procedures to be performed much more rapidly, resulting in less stress on the patient.

However, the use of such powered manipulators can impose certain safety problems. In particular, movement of the patient relative to the manipulator during the surgical or other interventional procedure can lead to serious trauma. Thus, it is generally thought that a patient must be under a general anesthesia or other paralytic during a procedure that is performed using a powered manipulator. Powered manipulators are generally thought as unsuitable for use in awake procedures. The use of a general anesthesia including neuro-muscular paralysis or the like, however, introduces more risk into the procedure and does not completely solve the problem of movement of the patient relative to the manipulator. For example, even when under a general anesthesia patient motion can be caused by respiration, cardio-ballistic motion, involuntary muscle motion (e.g., myoclonic jerks, tremors, twitching), peristalsis and inadvertent contact with the patient.

OBJECTS AND SUMMARY OF THE INVENTION

Accordingly, in view of the foregoing, a general object of the present invention is to provide an improved manipulator for use in surgical and other interventional medical procedures.

A more specific object of the present invention is to provide a surgical manipulator that can enhance the dexterity and precision of a surgeon/operator.

A further object of the present invention is to provide a surgical manipulator that provides enhanced patient safety by substantially reducing the likelihood of movement of the patient relative to the manipulator.

Another object of the present invention is to provide a surgical manipulator that is capable of achieving enhanced registration precision for image guided procedures or for use of anatomic waypoints (fiducials) identified during surgery.

These and other features and advantages of the invention will be more readily apparent upon reading the following description of a preferred exemplary embodiment of the invention and upon reference to the accompanying drawings wherein:

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENT

Figure 1:
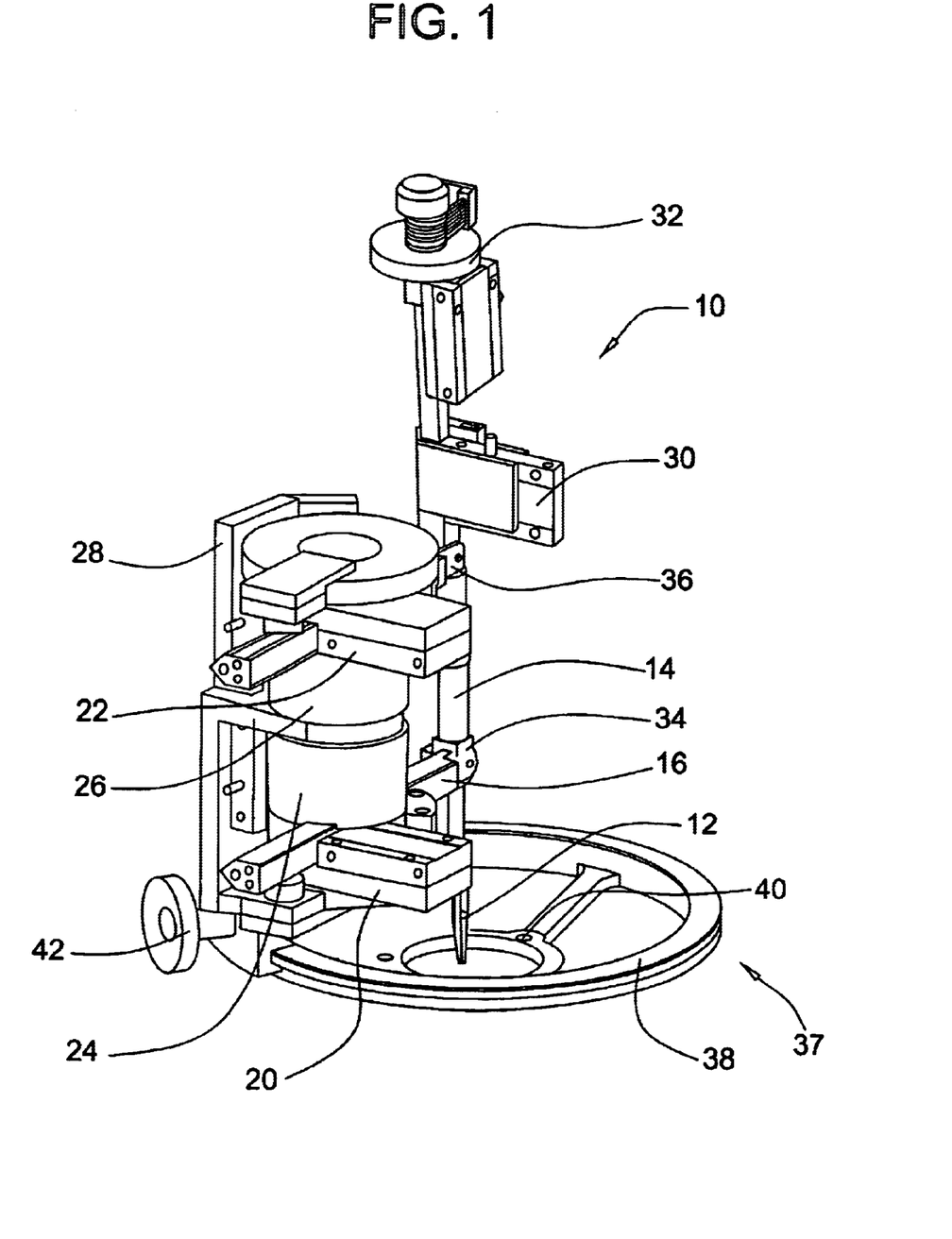
FIG. 1 is a front perspective view of an illustrative manipulator constructed in accordance with the teachings of the present invention.

Referring now more particularly to FIG. 1 of the drawings there is shown an illustrative embodiment of a surgical manipulator 10 constructed in accordance with the present invention. The illustrated manipulator 10 can interchangeably support and move a medical tool 12 with up to six degrees of freedom. As will be appreciated, the invention is not limited to any particular type of medical tool rather any suitable tool can be used with the manipulator including, but not limited to, needle holders, staple or clamp appliers, probes, scissors, forceps, cautery, suction cutters, dissectors, drills, lasers, ultrasonic devices and diagnostic devices. The tools can be reusable, limited reuse or disposable. If the medical tool has moving parts that are conventionally human powered, the manipulator 10 can be adapted to accommodate an actuator dedicated to powering the tool such as for example an electric, pneumatic or hydraulic actuator.

In order to provide dexterity enhancement for an operator/ surgeon in performing surgical and certain interventional radiology procedures, the manipulator 10 can be used as a slave robot in a master-slave robotic system. In such a system, a surgeon/operator provides position input signals to the "slave" manipulator via a master or haptic interface 13 which operates through a controller 15 or control console as in the schematic block diagram of FIG. 3. Specifically, through the use of an input device 17 on the haptic interface 13 such as a six degree of freedom tool handle with force feedback, joystick, foot pedal or the like, the surgeon indicates the desired movement of the tool 12 held by the manipulator 10. The haptic interface 13 relays these signals to the controller 15, which, in turn, applies various desired predetermined adjustments to the signals prior to relaying them to the slave manipulator. Any haptic interface having an equal or greater number of degrees of freedom (DOF) than the manipulator can be used to control the manipulator via the controller. Examples of haptic interfaces or masters which can be used with the present invention include the Freedom 6S available from MPB Technologies of Montreal, Canada, and other haptic interfaces commercially available from Sensable Technology of Cambridge, Mass. and Micro-Dexterity Systems of Albuquerque, N. Mex.

Figure 3:
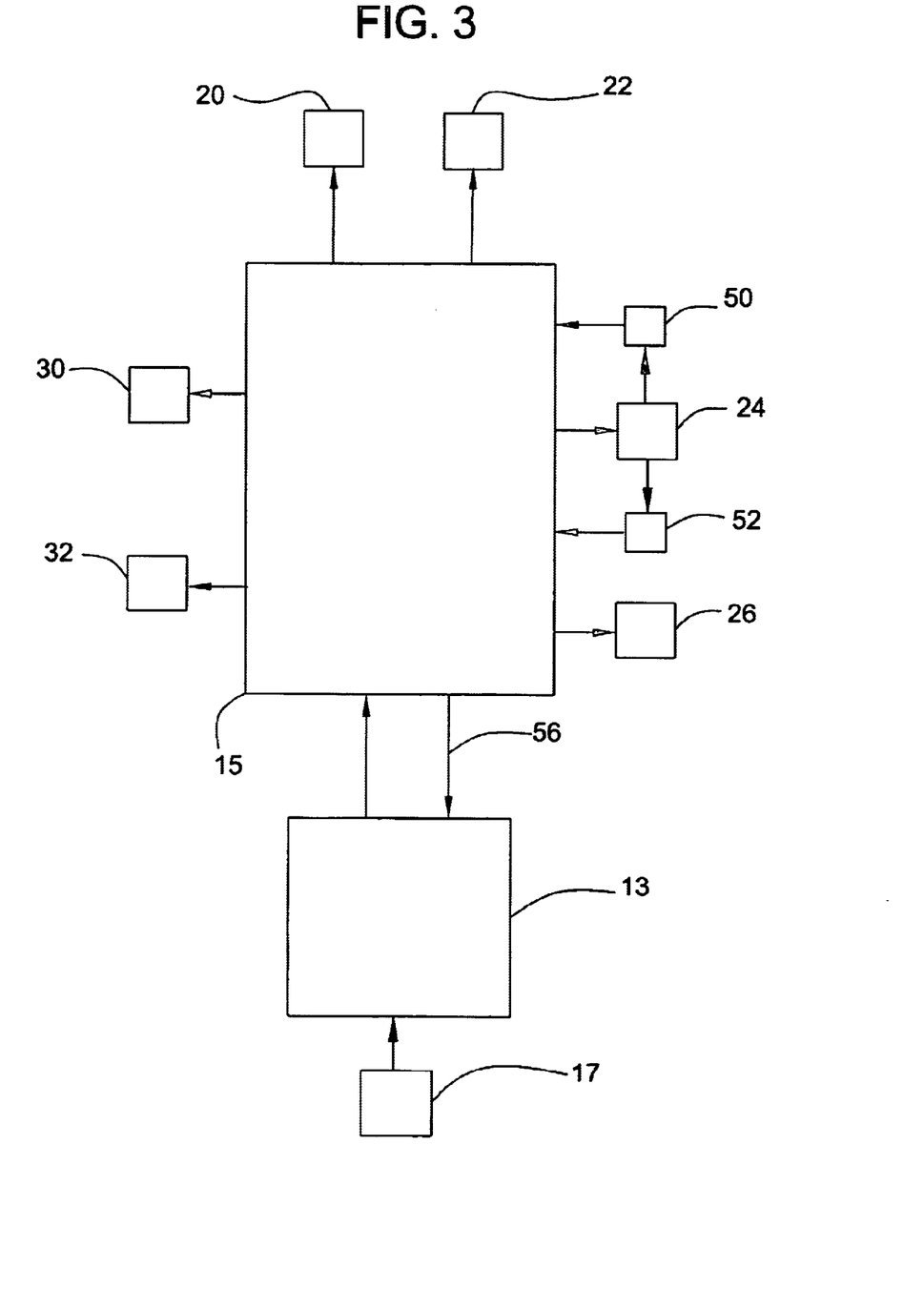
FIG. 3 is a block diagram of an illustrative control system for a manipulator constructed in accordance with the teachings of the present invention.

Based on the signals provided by the controller 15, the manipulator 10 executes the desired movement or operation of the tool 12. Thus, any desired dexterity enhancement can be achieved by setting up the controller 15 to perform the appropriate adjustments to the signals sent from the haptic interface 13. For example, this can be accomplished by providing the controller 15 with software which performs a desired dexterity enhancement algorithm. Software dexterity enhancement algorithms can include position scaling (typically downscaling), force scaling (up-scaling for bone and cartilage, downscaling for soft tissue), tremor filtering, gravity compensation, programmable position boundaries, motion compensation for aneurysms, velocity limits (e.g., preventing rapid movement into brain, nerve or spinal cord tissue after drilling through bone), and, as discussed in greater detail below, image referencing. These and other examples of possible algorithms are well known in the field of robotics and described in detail in published literature. An example of a suitable controller for use in the present invention is the Turbo PMAC available from Delta Tau Data Systems of Northridge, Calif.

Figure 2:
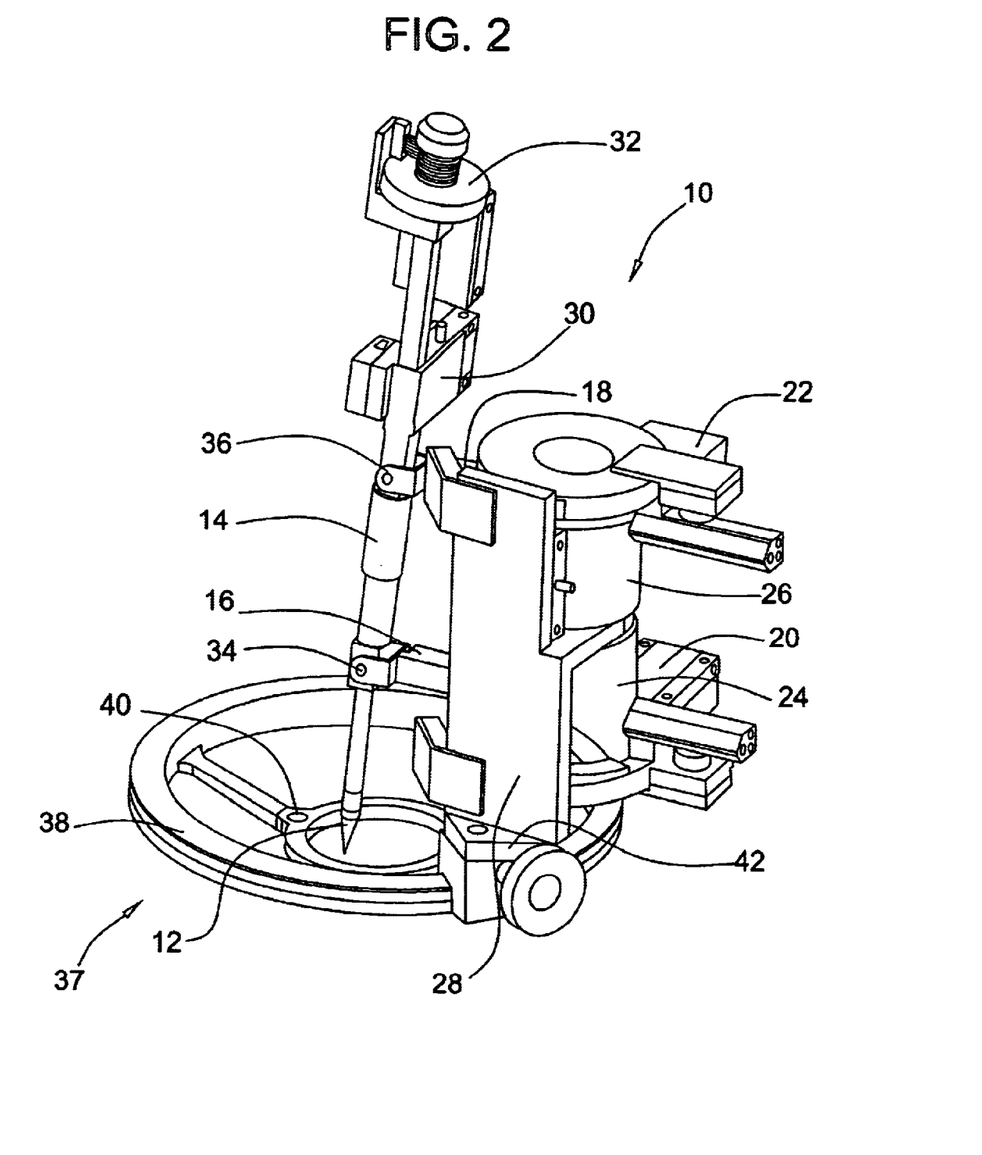
FIG. 2 is a rear perspective view of the manipulator of FIG. 1.

To permit movement of the tool 12 with, in the illustrated embodiment, six degrees of freedom, the tool is supported at a lower end of a tool support shaft 14 that can be translated in space via a system of rotary and linear actuators. More specifically, in the illustrated embodiment, the tool support shaft 14 is supported by a pair of, in this case, vertically spaced support or control arms 16, 18 each of which is independently movable via a respective linear actuator 20, 22 and a respective rotary actuator 24, 26. As shown in FIGS. 1 and 2, the linear actuator 20, 22 associated with each control arm 16, 18 is arranged so as to translate its respective control arm in a telescoping manner in a lengthwise direction. Each linear actuator 20, 22 is connected, in turn, to the output shaft of its corresponding rotary actuator 24, 26 so as to permit pivotal movement of the linear actuators 20, 22, and thereby the control arms 16, 18. In this case, the rotary actuators 24, 26 are arranged in stacked relation on a stationary support frame 28 such that their rotational axes are aligned. The rotary actuators, however, do not have to be in stacked relation as the two actuators 24, 26 can be independently located relative to each other.

Through the combination of the control arms 16, 18 and their corresponding linear 20, 22 and rotary actuators 24, 26, the tool support shaft 14 can be moved in space in four degrees of freedom. For example, the manipulator 10 can operate as a differential mechanism in that relatively large pitch and yaw angles of the tool support shaft 14 can be produced by rotating the rotary actuators 24, 26 for the two control arms 16, 18 in opposite directions and by moving the linear actuators 20, 22 for the two control arms in opposite directions. Additionally, the tool support shaft 14 can be moved like a cylindrical or polar coordinate robot by rotating the rotary actuators 24, 26 for the two control arms 16, 18 in the same direction and by moving the linear actuators 20, 22 for the two control arms in the same direction.

For moving the tool 12 in the lengthwise direction of the tool support shaft 14 and to provide for rotation of the tool about the longitudinal axis of the tool support shaft, two additional actuators are provided. In particular a linear actuator 30 is incorporated into the tool support shaft 14 which is operatively connected to the tool 12 (via a shaft or other means) so as to permit lengthwise movement of the tool 12 in a telescoping manner relative to the longitudinal axis of the tool support shaft 14. This lengthwise movement of the tool 12 relative to the tool support shaft 14 can be used to insert and withdraw the tool 12 from the body of a patient. The rotary movement of the tool 12 is produced by a rotary actuator 32 arranged, in this case, at the upper end of the tool support shaft 14 and operatively connected to the tool 12 (again, via a shaft or other suitable means) so as to enable rotation of the tool 12 about the longitudinal axis of the tool support shaft 14. The rotary movement of the tool 12 relative to the tool support shaft 14 can be useful when using axially asymmetric tools, such as for example, scissors which extend at an angle with respect to the tool support shaft.

To permit movement of the tool support shaft in the desired degrees of freedom each control arm 16, 18 is connected to the tool shaft 14 using an appropriate universal or gimbals joint. In the illustrated embodiment, the joints between the control arms and the tool support shaft comprise three degree of freedom Hookes type joints 34, 36. The joints between the tool support shaft and the control arms should provide six degrees of freedom to the tool shaft. This can also be accomplished by providing one joint which has two degrees of freedom and a second joint which has four degrees of freedom. Additionally, two joints each having two degrees of freedom could be used with the tool shaft itself supplying the two additional degrees of freedom to the tool as shown in FIGS. 1 and 2.

For sensing the positions of the various linear and rotary actuators 20, 22, 24, 26, 30, 32 and, in turn, the control arms 16, 18, joints 34, 36 and tool support shaft 14, the actuators can be equipped with position sensors 50. Each of the linear and rotary actuators can be in communication with the controller and the position sensors can provide position information in a feedback loop to the controller as shown in FIG. 3. For ease of reference, the position sensor for only one of the actuators is shown in FIG. 3. In one preferred embodiment, optical encoders are used to sense the positions of the various actuators, however, it will be appreciated that any number of different conventional position sensors can be used. Likewise, the various actuators can also be equipped with force sensors 52 (again, only one of which is shown in FIG. 3) for sensing the forces or torques applied by the actuators so as to enable a determination of the forces and torques applied to the tool support shaft 14. As shown in FIG. 3, this information can again be provided in a feedback control loop to the controller 15, for example to allow force feedback to the input device of the haptic interface (shown schematically as line 56). Of course, any known method for measuring forces and/or torques can be used, including, for example, foil type or semiconductor strain gauges or load cells.

Figure 4:
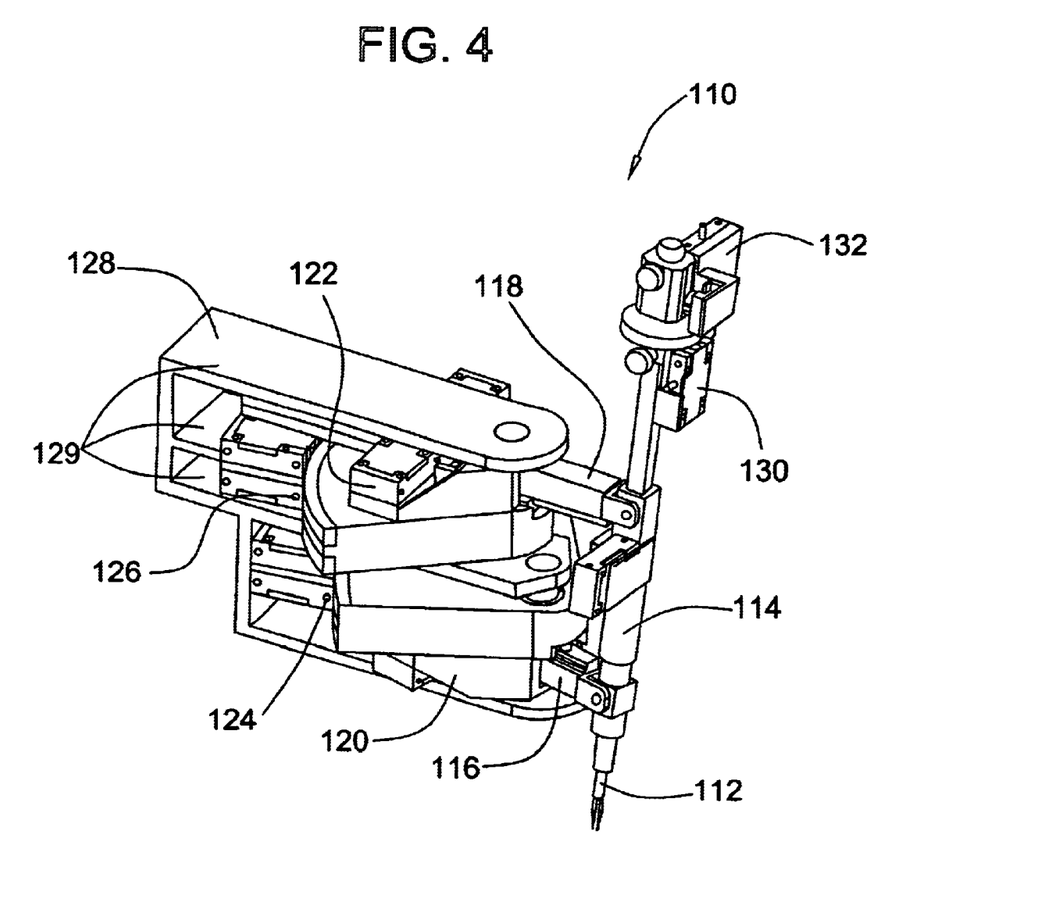
FIG. 4 is a perspective view of an alternative embodiment of a manipulator constructed in accordance with the present invention supporting a cautery/dissection tool.
Figure 5:
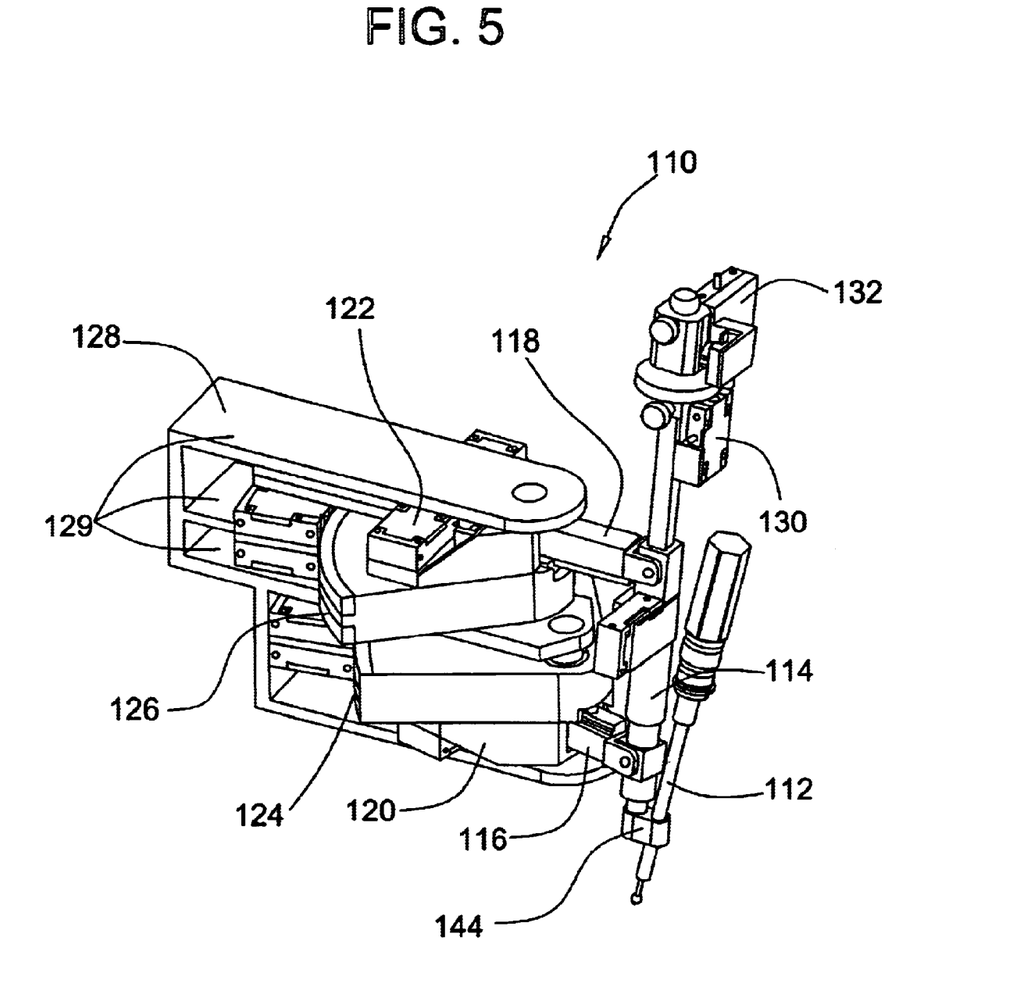
FIG. 5 is a perspective view of the manipulator of FIG. 4 supporting a drill.

Another embodiment of a manipulator according to the invention is shown in FIGS. 4 and 5 wherein components similar to those described above have been given similar reference numerals in the 100 series. The manipulator 110 of FIGS. 4 and 5 is very similar in configuration and operation to that of the manipulator 10 shown in FIGS. 1 and 2. In particular, the manipulator 110 shown in FIGS. 4 and 5 can move a tool 112 supported on a tool support shaft 114 in six degrees of freedom. To this end, as with the FIGS. 1 and 2 embodiment, the tool support shaft 114 is supported by a pair of spaced control arms 116, 118 each of which is independently movable via a respective linear actuator 120, 122 and a respective rotary actuator 124, 126. The linear actuator 120, 122 associated with each control arm 116, 118 translates the control arm in its lengthwise direction while the rotary actuator 124, 126 can pivot the linear actuator and, in turn, the control arm. The manipulator 110 shown in FIGS. 4 and 5 also includes a linear actuator 130 on the tool support shaft 114 which facilitates tool insertion and withdrawal and a rotary actuator 132 on the tool support shaft which facilitates tool roll.

Unlike the manipulator shown in FIGS. 1 and 2, the rotary actuators 124, 126 are supported on a frame 128 such that their rotary axes are not aligned. The support frame 128, in this case, includes upper, lower and intermediate support arms 129 between which the rotary and linear actuators are supported. The illustrated support frame 128 provides a relatively compact arrangement which can be readily connected to existing mounting arrangements as described in greater detail below.

FIGS. 4 and 5 also illustrate how the manipulator of the present invention can be used to support different tools. Specifically, as shown in FIG. 4, the manipulator 110 can support a tool 112, in the illustrated embodiment a cautery/dissection tool, which is arranged coaxially with the tool support shaft 114. Alternatively, as shown in FIG. 5, a tool 112 (in this instance, a drill) can be supported in offset relation from the tool support shaft 114 in order to accommodate, for example, an actuator for a powered tool. In this case, the tool 112 is connected to the tool support shaft 114 via a connector piece 144 which permits the tool to be moved in space with the support shaft. Moreover, by connecting the tool 112 to the pivotable and extensible lower end of the support shaft 114, the tool can also be moved via the tool insertion linear actuator 130 and the tool roll rotary actuator 132 on the support shaft. As will be appreciated, other arrangements can be used to mount the tool on the tool support shaft.

The construction and operation of the illustrated manipulators is similar to several of the manipulator embodiments disclosed in commonly assigned PCT Application Serial No. PCT/US99/27650 and corresponding U.S. application Ser. No. 09/856,453 entitled "Surgical Manipulator" the disclosure of which is incorporated herein by reference. As will be appreciated, while the illustrated manipulator geometry provides certain advantages including movement in six degrees of freedom, the present invention is not limited to a particular manipulator architecture or kinematic scheme. Instead, all that is necessary is to provide a manipulator that is capable of moving a tool in a desired number of degrees of freedom. For example, other manipulator architectures and kinematic schemes that can be used include a so-called dual SCARA scheme such as disclosed in PCT Application Serial No. PCT/US99/27650 and U.S. application Ser. No. 09/856, 453 and a dual planar scheme such as disclosed in U.S. Pat. Nos. 5,943,914 and 6,000,297 entitled respectively "Master-Slave Micromanipulator Apparatus" and "Master-Slave Micromanipulator Method". Moreover, while the illustrated embodiment only includes a single manipulator, two or more manipulators may be provided such as for procedures which require more than one hand or arm.

In accordance with one important aspect of the present invention, to substantially reduce the likelihood of patient movement relative to the manipulator 10, 110 during a surgical or other interventional procedure, thereby enhancing patient safety, the manipulator 10, 110 can include a mounting fixture which permits the manipulator to be fixed relative to at least a particular portion of a patient's body. The ability to fix the manipulator 10, 110 relative to the patient's body potentially eliminates the need for general anesthesia and muscle paralytics, and the associated medical risks, as well as the need for active compliance and/or passive backdriveabilty of the manipulator actuators.

To this end, in the embodiment illustrated in FIGS. 1 and 2, the actuator support frame 28 and, in turn, the tool support shaft 14 are connected to a mounting structure 37, in this instance a mounting ring 38, which can be mounted directly to skull or other body part of a patient. To facilitate attachment of the mounting ring 38 to, for instance, the skull of the patient, the mounting ring 38 includes mounting holes 40 (three in the illustrated embodiment) which can receive screws that attach the mounting ring to the skull. The actuator support frame 28 is connected to the mounting ring 38 by a clamping mechanism 42 which permits the actuator support frame 28 to be moved and locked into any given position around the perimeter of the mounting ring 38.

Figure 6:
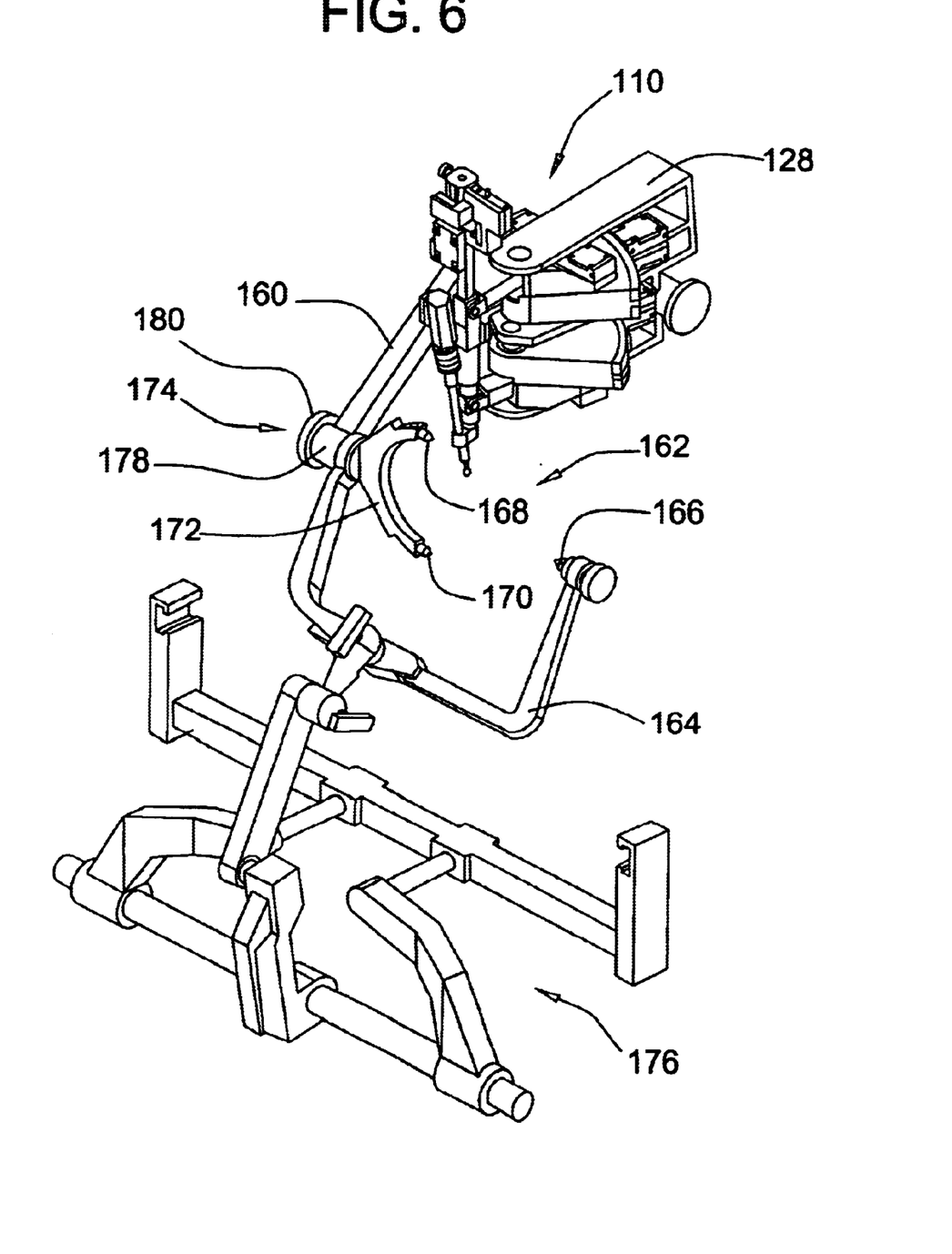
FIG. 6 is a perspective view of the manipulator of FIG. 4 mounted to a head clamp fixation system.
Figure 7:
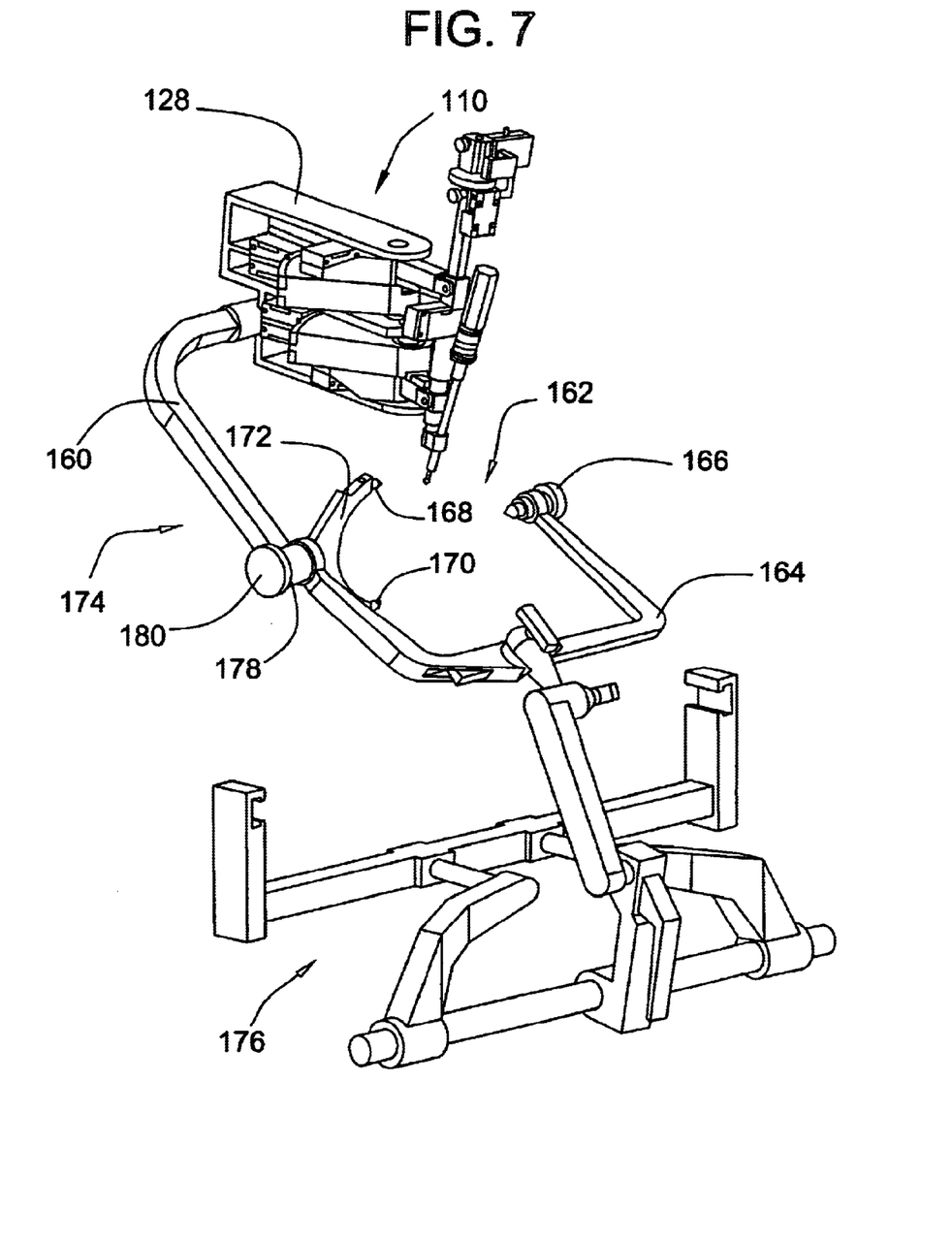
FIG. 7 is another perspective view of the manipulator of FIG. 4 mounted to a head clamp fixation system.

An embodiment of the invention in which the mounting structure includes a head clamp fixation system is illustrated in FIGS. 6 and 7. In the illustrated embodiment, an arm 160 is provided which interconnects the support frame 128 of the manipulator 110 of FIGS. 4 and 5 with a head clamp 162. The clamp 162 includes a C-shaped frame 164 which supports a first fixed head engaging pin 166 on one side and second and third head engaging pins 168, 170 on the opposite side. The second and third head engaging pins 168, 170 are supported on a clevis 172 that is rotatable relative to the frame 164 so as to allow a surgeon to adjust the angular position of the patient's head relative to the frame 164. The clamp 162 includes a rotation mechanism 174 for releasably locking the clevis 172 in a particular angular position relative to the frame 164. In the illustrated embodiment, the head clamp 162 is supported by a base unit 176 which allows the head clamp to be mounted to a medical table.

To ensure that the manipulator 110 remains fixed relative to the patient's head during adjustment of the position of the head, the arm 160 supporting the manipulator is tied into the rotation mechanism 174 of the clamp 162. In particular, the arm 160 is tied into a sleeve 178 which rotates with the clevis 172 as the angular position of the clevis is adjusted via a knob 180 on the rotation mechanism 174. Thus, the manipulator 110 remains fixed in the same position relative to the clevis 172, and in turn the patient's head, during any adjustment of the head. One example of a head clamp fixation system that can be used in the present invention is sold under the tradename MAYFIELD® by Ohio Medical Products of Cincinnati, Ohio (see, e.g. U.S. Pat. Nos. 5,269,034 and 5,546,663).

Of course, as will be appreciated by those skilled in the art, the present invention is not limited to any particular mounting fixture, but rather extends to any mounting fixture or system which allows the manipulator to be fixed relative to a desired portion of the patient's body. Nor is the present invention limited to being mountable to any particular location on the body. For instance, the manipulator 10 can be mounted to the skull (e.g., to perform neurosurgery, ear surgery or nasal surgery), the spine or other bony structures.

In order to permit mounting of the manipulator 10 to a patient, the manipulator 10 must have a relatively lightweight, compact design that has a relatively low inertia. Utilizing a lightweight, compact manipulator, helps alleviate the need to provide alternative support structures to relieve some of the weight exerted on the patient. While such support structures help reduce some of the stress on the patient caused by a manipulator, they can introduce significant inertia problems. To achieve the low mass and inertia, linear and rotary actuators having a relatively high force to mass ratio should be used in the manipulator. To this end, in one presently preferred embodiment of the invention, the linear and rotary actuators (20, 22, 24, 26, 120, 122, 124, 126) used in the manipulator comprise ultrasonic motors.

Besides a very high force to mass ratio, ultrasonic motors provide several other advantages over conventional stepper and DC motors. For example, ultrasonic motors have intrinsic braking when powered down at a force equivalent to its force when moving. This provides increased patient safety. Ultrasonic motors do not have heat dissipation issues and can be isolated electrically. Moreover, ultrasonic motors are very stable so as to permit use in clean rooms. Additionally, as compared to pneumatic actuators, actuators based on ultrasonic motors do not have overshoot problems when the tool is used to apply a force on a rigid body which then breaks free. One example of an ultrasonic motor suitable for use as either a linear or rotary actuator in the present invention is the SAW Ultrasonic Motor available from Nanomotion of Yokeneam, Israel (described in U.S. Pat. No. 5,453,653).

Alternatively, electrodynamic motors, hydraulic actuators or cable drives could also be used as the linear and rotary actuators on the manipulator. With respect to cable drives, either rotary or push-pull could be used. The prime movers for the cables can include air or fluid turbines or servo motors. When using cable drives, significant torque amplification would have to take place through the controller in order to compensate for the effects of backlash, windup, hysteresis and cable friction. If hydraulic actuators are used for the linear and rotary actuators, water, saline, or perfluorocarbon liquids can be used for hydraulic actuation to ensure patient safety in the event the hydraulic fluid comes into contact with the patient. Gear pumps or other suitable pumps like peristaltic, diaphragm, piston and venturi pumps can be used to control the flow of hydraulic fluid which is relatively incompressible compared to pneumatic actuation thereby avoiding overshoot problems. The actuators themselves can comprise, for example, piston/cylinder actuators (linear actuators), rotary vane, diaphragm and Bourdon tubes. To reduce static and dynamic friction, hydrostatic bearings can be used for the rotary and linear actuators. Other types of actuators having high force to mass ratios could also be used.

According to a further aspect of the present invention, the capability of fixing the manipulator 10, 110 relative to the patient also can provide enhanced precision of the registration of the manipulator 10 and the tool 12, 112 with respect to the patient. In particular, fixing the manipulator 10, 110 relative to the patient provides a constant mechanical reference so that images or constant subsets of image data acquired prior to or earlier in the procedure will remain in the same position relative to the manipulator 10, 110 as the procedure progresses.

With the embodiment of the invention shown in FIGS. 1 and 2, one method by which this can be accomplished is to perform preoperative imaging (e.g., magnetic resonance (MR) or X-ray) with the screws to be used to fix the manipulator 10 to the patient already implanted in the patient. The screws, which can be made of a MR or X-ray compatible material, can then act as reference points or fiducials in the images. At the time of surgery, the screws are used to define the mounting points for the manipulator mounting ring 38. Then, as the operation is performed, the position of the tool 12 can be rendered against the preoperative image. If desired, during the procedure, the image data against which the position of the tool 12 is rendered can be updated using, for example, CT, MR or the like.

As an alternative to performing the preoperative imaging with the mounting screws in place, the position of the tool 12, 112 and the mounting structure or the manipulator mechanism 10, 110 can be tracked relative to a pre- or intra-operative image using optical triangulation by integrating the manipulator into a StealthStation® system available from Medtronic of Minneapolis, Minn. or by using another three dimensional, six degree of freedom position sensing technology well known in the field of neuro, spine and other types of surgery such as, for example, electromagnetic tracking.

Figure 8:
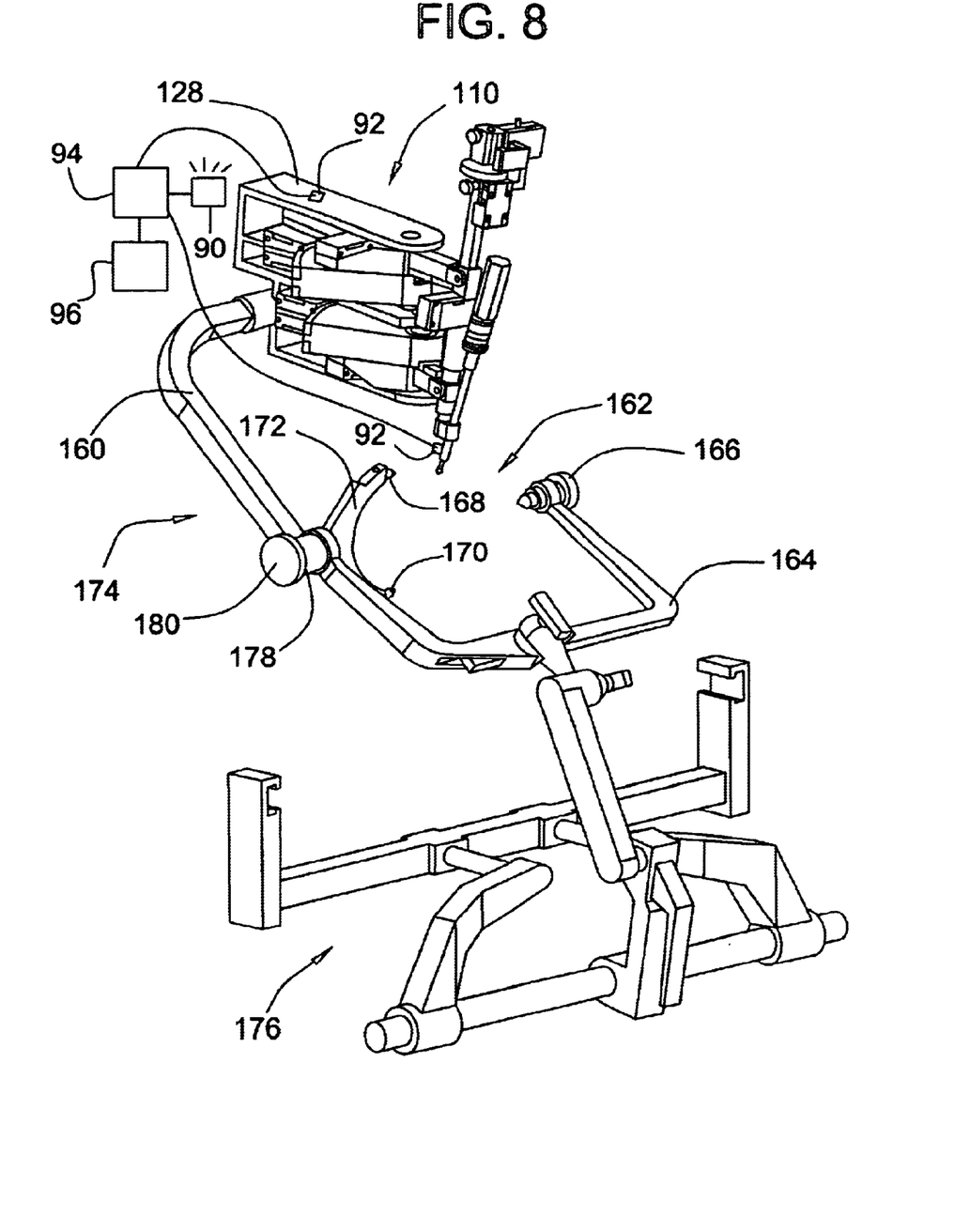
FIG. 8 is a perspective view of the manipulator of FIG. 4 further including a position tracking mechanism which is illustrated schematically.

An electromagnetic tracking or guidance system can be based, for example, on sensitivity to magnetic field strength, phase delay, phase versus position or pulse time of travel measurements to calculate a position and orientation of the tool with any degree of certainty from one to six degrees of constraint. One way in which this can be accomplished is to use an electromagnetic field generator 90 comprising, for example, three orthogonally disposed coil loops which are capable of producing a multidimensional field in three dimensions such as shown schematically in FIG. 8. The magnetic fields produced by each of the three coils can be mutually distinguishable from one another via either phase, frequency or time multiplexing. Remote sensors 92 for detecting the field generated by the field generator, which could comprise three orthogonally disposed dipole sensing elements, can be placed on the tool and in other locations such as on the manipulator as shown in FIG. 8. The position of the remote sensors 92 relative to the field generator 90 can then be monitored and correlated with stored preoperative images by a position detection controller 94 and shown on a display 96. The position detection controller could be the same controller used to control movement of the manipulator or a different controller.

These types of electromagnetic positioning techniques are used with global positioning systems, radar, resolvers and other electromagnetic position determining systems. Such an electromagnetic tracking or guiding system is not limited to use with the particular manipulator configurations disclosed herein but rather can be used to track and/or guide any type of tool that is supported and moved a manipulator or robot in one or more degrees of freedom. Electromagnetic position systems that can be adapted for use with the present invention are available from Visualization Technologies of Boston, Mass. (see, e.g., U.S. Pat. Nos. 5,676,673 and 5,829,444), UltraGuide of Lakewood, Colo. and Polhemus of Colchester, Vt.

During a medical procedure, it is possible that the manipulator 10, 110 and haptic interface 13 will be tilted or rotated with respect to one another such that they are in different orientations with respect to the patient. For example, the patient may be placed in a specific orientation in order to allow viewing of the surgical site with, for example, a microscope. The manipulator 10, 110 will then be arranged so as to provide the best access to the surgical site without obscuring the view of the surgical site. The haptic interface, in turn, will be oriented to provide a good ergometric and comfortable position for the surgeon's hand arm. In such a case, it is likely that the coordinate reference frames of the manipulator and haptic interface will be skewed from one another and with respect to the patient.

The surgeon operating the manipulator through the haptic interface will be observing the tool 12 held by the manipulator 10, 110 and the surgical site during a surgical procedure. Accordingly, the position tracking system (which can be electromagnetic, optical or any other suitable system) and accompanying position detection controller can be adapted to specifically locate the manipulator, haptic interface and patient and to perform any necessary translations of movements in the haptic interface reference frame and manipulator reference frame with respect to the coordinate reference frame of the patient. These translations can be performed, for example, by a translation algorithm executed by the controller and can coordinate movement of the haptic interface input device and the tool held by the manipulator with respect to the patient's frame of reference regardless of the orientation of the haptic interface and manipulator relative to each other and the patient. Thus, when a surgeon moves his hand forward straight and level using the haptic interface, the medical tool held by the manipulator will also move in the same trajectory even if the manipulator is mounted in a skewed orientation relative to the patient.

In accordance with yet another aspect of the present invention, the manipulator 10, 110 can be constructed so as to be compatible with an MR or X-ray environment. This would allow the manipulator 10 to operate within and during a MR imaging or other X-ray procedure, thereby enabling the surgeon to visualize, for example, the target tissue, normal tissue and the tool 12, 112 in the same real-time or near real-time imaging environment. In order to allow the manipulator 10, 110 to operate in a MR environment, the manipulator must be constructed entirely of MR imaging compatible materials such as certain metals, plastics, glass and ceramics. Additionally, the linear and rotary actuators 20, 22, 24, 26, 120, 122, 124, 126 used in the manipulator must also be compatible with MR imaging. In this regard, both ultrasonic and hydraulic actuators have the additional advantage of being MR compatible. In order to permit the manipulator 10, 110 to be used while performing X-ray imaging, certain components of the manipulator can also be made of radiolucent materials such as plastics, graphite, ceramics and glass. The position encoders and force sensors associated with the actuators also can be made MR and/or X-ray imaging compatible. For example, fiber optic connected sine-cosine optical encoders, such as are commercially available from MicroE, Renishaw or Computer Optical Products, can be used for the position encoding and piezoelectric strain gauges for the force sensing.

From the foregoing, it will be appreciated that the present invention provides a lightweight and compact patient mountable manipulator that can be used in a master-slave robotic system to enhance the dexterity of a operator/surgeon. The capability of fixing the manipulator relative to the body of a patient provides enhanced safety by substantially reducing the likelihood of trauma caused by unintentional movement of the patient relative to the manipulator. Moreover, fixing the manipulator relative to the body of the patient provides a very precise mechanical reference which facilitates tracking of the medical tool with respect to a pre- and/or intra-operative image. The manipulator can be constructed such that it can be operated while performing MR or X-ray imaging so as allow to the position of the tool to be referenced to a real-time or near real-time image. Thus, the lightweight, compact manipulator of the present invention and its capability of operating in up to six degrees of freedom in a relatively large workspace makes the invention suitable for use in any number of different medical procedures including, for example, neurosurgery, ear surgery, sinus surgery and spine surgery.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A manipulator for use in performing medical procedures on a body of a patient, the manipulator comprising:
   a first tool support arm;
   a second tool support arm;
   a medical tool pivotably supported by the first and second support arms;
   wherein the support arms are movable independently of each other to manipulate the tool with at least one degree of freedom;
   a support frame which carries the first and second support arms such that the first and second support arms are movable with respect to the support frame; and
   a mounting structure which carries the support frame and is capable of fixing the support frame relative to at least a portion of the body of the patient.

2. A manipulator according to claim 1 wherein the mounting structure is mountable to the portion of the body of the patient.

3. A manipulator according to claim 2 wherein the mounting structure comprises a mounting ring which is mounted to the support frame.

4. A manipulator according to claim 3 wherein the mounting structure is mountable to the portion of the body of the patient by fasteners received in a plurality of mounting apertures in the mounting ring.

5. A manipulator according to claim 3 wherein the support frame is mounted to the mounting ring such that the position of the support frame relative to the mounting ring is selectively adjustable.

6. A manipulator according to claim 5 wherein the support frame is releasably lockable in a desired position relative to the mounting ring.

7. A manipulator according to claim 1 wherein the mounting structure comprises a head clamp.

8. A manipulator according to claim 1 wherein the mounting structure is further capable of fixing the portion of the patient's body relative to a third support structure.

9. A manipulator according to claim 8 wherein the third support structure comprises an operating table.

10. A manipulator according to claim 8 wherein the mounting structure comprises a head clamp fixation system.

11. A manipulator according to claim 10 wherein the head clamp fixation system includes a head clamp which is selectively adjustable to allow adjustment of the orientation of the head of a patient relative to the third support structure.

12. A manipulator according to claim 11 wherein the support frame is fixed relative to the head clamp.

13. A manipulator according to claim 1 wherein the first support arm is pivotable about a first axis by a first rotary actuator and the second support arm is pivotable about a second axis by a second rotary actuator.

14. A manipulator according to claim 13 wherein the first axis and the second axis are aligned with each other.

15. A manipulator according to claim 13 wherein the first axis and the second axis are offset from each other.

16. A manipulator according to claim 13 wherein the rotary actuators comprise electrodynamic motors.

17. A manipulator according to claim 13 wherein the rotary actuators comprise ultrasonic motors.

18. A manipulator according to claim 1 wherein the first support arm includes a first linear actuator for moving the first support arm in a lengthwise direction and the second support arm includes a second linear actuator for moving the second support arm in a lengthwise direction.

19. A manipulator according to claim 18 wherein the first and second linear actuators comprise electrodynamic linear motors.

20. A manipulator according to claim 18 wherein the first and second linear actuators comprise ultrasonic linear motors.

21. A manipulator according to claim 13 wherein the first support arm includes a first linear actuator for moving the first support arm in a lengthwise direction perpendicular to the first rotational axis and the second support arm includes a second linear actuator for moving the second support arm in a lengthwise direction perpendicular to the second rotational axis.

22. A manipulator according to claim 1 further including a tool support member pivotably supported by the first and second arms and on which the medical tool is carried.

23. A manipulator according to claim 22 wherein the tool support member includes a linear actuator for moving the medical tool along a linear path relative to the tool support member.

24. A manipulator according to claim 22 wherein the tool support member includes a rotary actuator for rotating the medical tool relative to the tool support member.

25. A manipulator according to claim 1 wherein the first and second support arms and the medical tool are constructed of magnetic resonance imaging compatible materials.

26. A manipulator according to claim 1 wherein the first and second support arms and the medical tool are constructed of radiolucent materials.

27. A manipulator according to claim 1 further including a haptic interface which communicates with a controller that directs movement of the first and second support arms.

28. A manipulator according to claim 27 wherein the haptic interface is adapted to receive manually input position information from an operator and communicate position signals based on the position information to the controller and the controller is adapted to make predetermined adjustments to the position signals prior to directing movement of the first and second arms.

29. A method of performing a medical procedure on a body of a patient comprising the steps of:

pivotably supporting an elongated tool support having a medical tool mounted thereon by first and second independently movable manipulator arms which are carried by a manipulator support frame;

fixing the manipulator support frame relative to the portion of the body of the patient with a mounting structure; and moving the manipulator arms in order to move the medical tool.

30. A method according to claim 29 further including the step of inputting position signals for the medical tool through a haptic interface which is manually operable by an operator.

31. A method according to claim 30 further the step of directing the movement of the first and second manipulator arms based on the position signals using a controller.

32. A method according to claim 31 further including the step of performing predetermined adjustments to the position signals using the controller prior to directing movement of the first and second manipulator arms.

33. A method according to claim 32 wherein the step of performing predetermined adjustments includes enhancing the dexterity of the haptic interface operator.

34. A method according to claim 33 further including the step of tracking the position of the medical tool relative to the portion of the patient's body.

35. A method according to claim 34 further including the steps of forming an image of the portion of the patient's body and displaying the position of the medical tool relative to the portion of the patient's body in the image.

36. A method according to claim 35 further including the step of updating the image of the portion of the patient's body after moving the medical tool.

37. A method according to claim 34 wherein the step of tracking the position of the medical tool is performed using optical triangulation.

38. A method according to claim 34 wherein the step of tracking the position of the medical tool is performed using electromagnetic tracking.

39. A method according to claim 29 further including the step of forming an image of the medical tool and the portion of the patient's body after moving the medical tool.

40. A method according to claim 30 further including the steps of:

establishing a plurality of reference points on the portion of the patient's body;

forming an image of the portion of the patient's body which includes the reference points; and fixing the mounting structure to the patient's body in a predetermined position relative to the reference points.

41. A method according to claim 40 further including the step of tracking the position of the medical tool relative to the reference points.

42. A method according to claim 41 further including the step of rendering the position of the medical tool on the image.

43. A method according to claim 32 wherein the position signals are input through a movable input device of the haptic interface and the step of performing predetermined adjustments includes coordinating movement the input device and the medical tool based on the orientation of the manipulator support frame relative to the haptic interface.

44. A manipulator for use in performing medical procedures on a portion of a body of a patient, comprising:

a medical tool;

a positioning mechanism which carries the medical tool, the positioning mechanism being capable of moving the tool with at least one degree of freedom;

an electromagnetic field generator for producing a multidimensional electromagnetic field in three mutually distinguishable dimensions;

a first remote field sensor carried by the tool for detecting the multidimensional electromagnetic field; and a second remote field sensor carried by the manipulator support frame or the body of the patient for detecting the multidimensional electromagnetic field; and a position detection controller in communication with the first and second remote field sensors for determining a position of the first remote field sensor relative to the second remote field sensor in three dimensions.

45. A manipulator according to claim 43 further including an output display in communication with the position detection controller for displaying the position of the first remote field sensor relative to an image of the portion of the body of the patient.

46. A manipulator according to claim 44 wherein the positioning mechanism comprises first and second arms which pivotably support the medical tool and which are movable independently of each other.

47. A manipulator according to claim 44 further including a haptic interface which communicates with a manipulator controller that directs movement of the positioning mechanism.

48. A manipulator according to claim 46 wherein the haptic interface is adapted to receive manually input position information from an operator and communicate position signals based on the position information to the manipulator controller and the manipulator controller is adapted to make predetermined adjustments to the position signals prior to directing movement of the positioning mechanism.

49. A method for performing a medical procedure on a body of a patient comprising the steps of:

supporting a medical tool with a manipulator capable of moving the medical tool with at least one degree of freedom;

mounting the manipulator relative to the patient's body;

mounting a haptic interface relative to the patient's body;

tracking the orientation of the manipulator, the orientation of the haptic interface and the position of the medical tool relative to a predetermined frame of reference using a three dimensional, six degree of freedom position detection system;

inputting position signals for the medical tool through movement of an input device of the haptic interface;

adjusting the position signals based on the orientation of the manipulator relative to the haptic interface to coordinate movement of the input device and the medical tool in the predetermined frame of reference; and operating the manipulator based on the translated position signals to move the medical tool.

50. A method according to claim 49 wherein the step of tracking the orientation of the manipulator, the orientation of the haptic interface and the position of the medical tool is performed using optical triangulation.

51. A method according to claim 49 wherein the step of tracking the orientation of the manipulator, the orientation of the haptic interface and the position of the medical tool is performed using electromagnetic tracking.

52. A manipulator for use in performing medical procedures on a portion of a body of a patient, comprising:

a medical tool;

a controller;

a positioning mechanism in communication with the controller which carries the medical tool, the positioning mechanism being capable of moving the tool with at least one degree of freedom;

a haptic interface in communication with the controller for receiving position information through a movable input device and transmitting position signals to the controller based on the position information;

a position tracking system in communication with the controller for tracking the position of the medical tool and the orientations of the positioning mechanism and the haptic interface relative to a predetermined frame of reference; and wherein the controller is adapted to adjust the position signals received from the haptic interface based on the orientation of the haptic interface relative to the positioning mechanism as tracked by the position tracking system so as to coordinate movement of the input device and the medical tool in the predetermined frame of reference and to direct the positioning mechanism to move the medical tool based on the adjusted positioning signals.

53. The manipulator according to claim 52 wherein the position tracking system uses optical triangulation.

54. The manipulator according to claim 52 wherein the position tracking system uses electromagnetic tracking.

55. The manipulator according to claim 52 wherein the positioning mechanism comprises first and second arms which pivotably support the medical tool and are movable independent of each other.

* * * * *